(12) United States Patent
Mitchell et al.

(10) Patent No.: US 10,155,774 B2
(45) Date of Patent: Dec. 18, 2018

(54) SEMICONDUCTING POLYMERS

(71) Applicant: MERCK PATENT GESELLSCHAFT MIT BESCHRANKTER HAFTUNG, Darmstadt (DE)

(72) Inventors: William Mitchell, Chandler's Ford (GB); Steven Tierney, Southampton (GB); Changsheng Wang, Durham (GB); Nicolas Blouin, Southampton (GB)

(73) Assignee: MERCK PATENT GESELLSCHAFT MIT BESCHRANKTER HAFTUNG, Darmstadt (DE)

( * ) Notice: Subject to any disclaimer, the term of this patent is extended or adjusted under 35 U.S.C. 154(b) by 0 days.

(21) Appl. No.: 14/829,698

(22) Filed: Aug. 19, 2015

(65) Prior Publication Data

US 2015/0353575 A1 Dec. 10, 2015

Related U.S. Application Data

(62) Division of application No. 13/578,931, filed as application No. PCT/EP2010/007887 on Dec. 22, 2010, now Pat. No. 9,365,585.

(30) Foreign Application Priority Data

Feb. 15, 2010 (EP) .................................... 10001528

(51) Int. Cl.
| | | |
|---|---|---|
| C07D 495/04 | (2006.01) | |
| C09K 19/34 | (2006.01) | |
| C08G 61/12 | (2006.01) | |
| C09K 19/38 | (2006.01) | |
| C09K 19/40 | (2006.01) | |
| H01L 51/00 | (2006.01) | |
| H01L 51/42 | (2006.01) | |
| C09K 19/04 | (2006.01) | |

(52) U.S. Cl.
CPC ......... *C07D 495/04* (2013.01); *C08G 61/126* (2013.01); *C09K 19/3477* (2013.01); *C09K 19/3491* (2013.01); *C09K 19/3497* (2013.01); *C09K 19/38* (2013.01); *C09K 19/40* (2013.01); *H01L 51/0036* (2013.01); *H01L 51/0043* (2013.01); *C08G 2261/124* (2013.01); *C08G 2261/1428* (2013.01); *C08G 2261/3243* (2013.01); *C08G 2261/414* (2013.01); *C08G 2261/91* (2013.01); *C09K 2019/0448* (2013.01); *C09K 2019/0496* (2013.01); *H01L 51/0037* (2013.01); *H01L 51/4253* (2013.01); *Y02E 10/549* (2013.01)

(58) Field of Classification Search
CPC ................ C07D 495/04; C08G 61/126; C09K 19/3477; C09K 19/3491; C09K 19/3497; C09K 19/38; C09K 19/40; H01L 51/0036; H01L 51/0043
See application file for complete search history.

(56) References Cited

U.S. PATENT DOCUMENTS

| | | | |
|---|---|---|---|
| 3,268,545 A | 8/1966 | Litt et al. | |
| 3,336,328 A | 8/1967 | Gustav | |
| 6,355,773 B1 | 3/2002 | Weinfurtner et al. | |
| 7,372,071 B2 | 5/2008 | Li et al. | |
| 7,524,922 B2 | 4/2009 | Heeney et al. | |
| 2003/0209692 A1 | 11/2003 | Farrand et al. | |
| 2005/0082525 A1* | 4/2005 | Heeney | C07D 495/04 257/40 |
| 2005/0193504 A1* | 9/2005 | Glenn, Jr. | A61K 8/49 8/405 |
| 2005/0258398 A1 | 11/2005 | Kobayashi et al. | |
| 2007/0235721 A1 | 10/2007 | Li et al. | |
| 2007/0235722 A1* | 10/2007 | Li | H01L 51/0035 257/40 |
| 2007/0238855 A1 | 10/2007 | Li et al. | |
| 2009/0314997 A1 | 12/2009 | Heeney et al. | |
| 2011/0124822 A1 | 5/2011 | Yu et al. | |

FOREIGN PATENT DOCUMENTS

| | | |
|---|---|---|
| CN | 101495487 A | 7/2009 |
| EP | 1357163 | 10/2003 |
| EP | 1524286 | 4/2005 |
| EP | 1843410 | 10/2007 |
| EP | 2207218 | 7/2010 |
| JP | 10340786 | 12/1998 |
| JP | 2000281629 A | 10/2000 |
| JP | 2005154371 | 6/2005 |
| WO | 2008-011957 | 1/2008 |
| WO | 2008011957 | 1/2008 |
| WO | 2008121585 A1 | 10/2008 |
| WO | 2009030329 A1 | 3/2009 |
| WO | 2009038120 A1 | 3/2009 |
| WO | 2009118086 A1 | 10/2009 |
| WO | 2010-008672 | 1/2010 |
| WO | 2011/098113 A2 | 8/2011 |

OTHER PUBLICATIONS

ACS Registry 863993-68-4, 2005.*
Bertanek, E. et al., "Bromination and subsequent ozonisation of Ethyl 2,6-dimethyl-benzo [1,2-b, 4.5-b'] difuran-3,7-dicarboxylate," Acta Chemica Scandinavica, 1961, No. 15, pp. 429-430.
English translation of Grynev, A. N. et al., "VIII The Condensation of chloro and 2,3-dichloro-π-benzoquinone with acetoacetic and benzoylacetic esters," Zhurnal Obshchhei Khimii, Jan. 1, 1956, vol. 26, No. 2, pp. 561-564.

(Continued)

*Primary Examiner* — Amina S Khan
(74) *Attorney, Agent, or Firm* — Millen White Zelano and Branigan, PC

(57) ABSTRACT

The invention relates to novel polymers containing repeating units based on benzodithiophene or derivatives thereof, monomers and methods for their preparation, their use as semiconductors in organic electronic (OE) devices, especially in organic photovoltaic (OPV) devices, and to OE and OPV devices comprising these polymers.

4 Claims, 1 Drawing Sheet

(56) References Cited

OTHER PUBLICATIONS

English translation of Ikuta, M. et al., "Communication from the Chemical Laboratory of Clark University," Journal fuer praktische Chemie, 1981, vol. 45, No. 1, pp. 65-83.

Hegedus, L. S. et al., "Synthesis of 2,5-Distributed 3,6-Diamino-1,4-benzoquinones," J. Org. Chem., 1982, vol. 47, pp. 2607-2613.

International Search Report for PCT/EP2010/007887, Date of the actual completion of the international search: May 11, 2011, dated Aug. 8, 2011.

Jayakannan, M. et al., "Mechanistic aspects of the Suzuki Polycondensation of Thiophenebisboronic Derivatives and Diiodobenzenes Analyzed by MADI-TOF Mass Spectrometry," Macromolecules, 2001, vol. 34, pp. 5386-5393.

Katz, H. E. et al., "Synthetic Chemistry for ultrapure, processable, and high-mobility organic transistor semiconductors," Acc. Chem. Res., 2001, vol. 34, pp. 359-369.

Liang, Y. et al., "Development of new semiconducting polymers for high performance solar cells," Journal of the American Chemical Society, vol. 131, pp. 56-57.

Osman, A. M. et al., "2-Arylnaphthoxazoles and Some Other Condensed Oxazoles," Journal of Organic Chemistry, 1962, vol. 27, No. 2, pp. 558-561.

Osman, A. M. et al., "Benzdioxazoles," Journal of the American Chemical Society, vol. 79, No. 4, pp. 966-968.

Osman, A. M. et al., "Heterocyclic compounds. Part 1. Synthesis of Benzodioxazoles and benzobisthiazoles and preparation of new dyes therefrom," U. A. R. J. Chem., 1971, vol. 14, No. 5, pp. 475-492.

Osowska, K. et al., "Supramolecular organization of extended benzobisoxazole cruciforms," The Royal Society of Chemistry—Chem Commun., 2010, vol. 46, pp. 4276-4278.

Pomerantz, M. et al., "Poly(benzo[1,2-B:4,5-b']dithiophene-4,9-diylvinylene). Synthesis, Properties, and Electronic Structure of a New Dithiophene-Fused p-Phenylenevinylene Conducting Polymer," Macromolecules, 1994, vol. 27, pp. 7478-7485.

Rao, D. S. et al., "Thiophenes & Thiapyrans: Part XV-Benzo-(I:2-b, 4:3-b')-dithiophene & Benzo-(I:2-b, 4:5-b')- dithiophene," J. Sci., Indust. Res., 1957, vol. 16B, pp. 65-68.

Roncali, J. et al., "Synthetic Principles for Bandgap control in linear π-conjugated systems," Chem. Rev. 1997, vol. 97, pp. 173-205.

Wang, C. et al., "Linear C2-symmetric polycyclic benzodithiophene: efficient, highly diversified approaches and the optical properties," Tetrahedron Letters, 2005, vol. 46, pp. 8153-8157.

Toyo Ink Mfg Co Ltd., "Organic electroluminescent element material and organic electroluminescent element using it," Patent Abstracts of Japan, Publication Date: Dec. 22, 1998; English Abstract of JP-10 340786.

Japan Science & Technology Agency, "New benzodichalcogenophene derivative, method for producing the same and organic semiconductor device produced by using the same," Patent Abstracts of Japan, Publication Date: Jun. 16, 2005; English Abstract of JP-2005 154371.

English Translation of Office Action for related Chinese Patent Application No. 201080063896.8 dated Feb. 21, 2012.

English Abstract of WO2009038120, Publication Date: Mar. 26, 2009.

English Abstract of JP2000281629, Publication Date: Oct. 10, 2000.

Korean Grounds for Rejection dated Mar. 17, 2017 for corresponding Korean Application No. 10-2012-7023849.

\* cited by examiner

SEMICONDUCTING POLYMERS

FIELD OF THE INVENTION

The invention relates to novel polymers containing repeating units based on benzodithiophene or derivatives thereof, monomers and methods for their preparation, their use as semiconductors in organic electronic (OE) devices, especially in organic photovoltaic (OPV) devices, and to OE and OPV devices comprising these polymers.

BACKGROUND OF THE INVENTION

In recent years there has been growing interest in the use of polymers for electronic applications. One particular area of importance is organic photovoltaics (OPV). Polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies up to 7%.

A class of polymers that is achieving the highest efficiencies in polymer based photovoltaic devices is based on units that have a high quinoidal contribution. Poly(thiophene), for example, has both an aromatic and a quinoidal contribution as shown below:

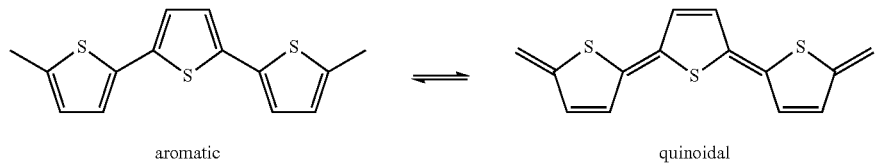

aromatic     quinoidal

A quinoidal structure reduces the torsion between adjacent rings, which results in a more planar polymer backbone leading to an extension of the effective conjugation length. It is generally observed in conjugated polymers that an increase in the conjugation length results in a decrease of the bandgap, leading to a higher degree of absorbed incident light.

The quinoidal state can be stabilised by fusing an aromatic ring to the thiophene backbone. The fused ring is only fully aromatic when the backbone is in the quinoidal state. This means there is a strong desire for the polymer to be in the quinoidal state. Previous work has demonstrated that the bandgap can be reduced by using a benzo-fused thiophene, as in poly(isothianaphthene) (1) shown below [see J. Roncali, *Chem. Rev.*, 1997, 97, 173] or by using a thieno[3,4-b]thiophene, as in poly(thieno[3,4-b]thiophene-benzo[1,2-b:4,5-b']dithiophene) (2) shown below, wherein R' is an octyloxy group and R" is a dodecyloxycarbonyl group [see Y. Liang; Y. Wu; D. Feng; S.-T. Tsai; H.-J. Son; G. Li; L. Yu, *J. Am. Chem. Soc.*, 2009, 131 (1), 56-57].

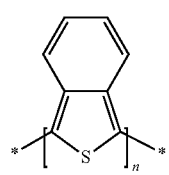
(1)

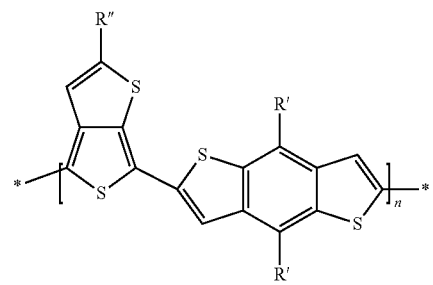
(2)

However, poly(isothianapthene) (1), which is either prepared chemically or electrochemically suffers from insolubility due to a lack of solubilising functionality. Soluble alkylated poly(isothianapthenes) have also been discussed by J. Roncali, *Chem. Rev.*, 1997, 97, 173, however, there is no hint to the semiconducting properties of this or similar materials, or that this or similar polymers could be suitable for use in OPV devices.

Regarding polymers based on benzo[1,2-b:4,5-b']dithiophene units (hereinafter also referred to as "BDT"), like poly(thieno[3,4-b]thiophene-benzo[1,2-b:4,5-b']dithiophene) (2), these have certain drawbacks with respect to their polymerisation methods as usually employed.

Usually, such polymers are synthesized by an organometallic catalyzed aryl-aryl coupling reaction of the monomeric units. Typically used coupling reactions include e.g. Yamamoto coupling of the monomers with reactive halide groups (see e.g. Yamamoto, T.; Morita, A.; Miyazaki, Y.; Maruyama, T.; Wakayama, H.; Zhou, Z. H.; Nakamura, Y.; Kanbara, T.; Sasaki, S.; Kubota, K. *Macromolecules* 1992, 25, 1214-1223, and Yamamoto, T.; Takimiya, K. *J. Am. Chem. Soc.* 2007, 129, 2224-2225), or Suzuki coupling of the monomers with reactive halide and/or boronic acid or boronic acid ester groups (see e.g. Schlüter, A. D. *J. Polym. Sci., Part A: Polym. Chem.* 2001, 39, 1533-1556), or Stille coupling of the monomers with reactive organotin groups (see e.g. Bao, Z.; Chan, W. K.; Yu, L. *J. Am. Chem. Soc.* 1995, 117, 12426-12435).

However, when preparing polymers from thiophene-containing monomers, like thieno[3,4-b]thiophene-2,6-diyl, via a Suzuki coupling reaction where the thiophene rings are functionalized with boronic acid or boronic acid ester groups, an undesired side-reaction called deboronation can occur to a significant degree [see M. Jayakannan, J. L. J. van Dongen, R. A. J. Janssen, *Macromolecules*, 2001, 34, 5386]. Deboronation prematurely halts the polymerization and leads to the formation of low molecular weight polymer chains which lack the requisite physical properties. On the other hand, Stille coupling, which was reported in the literature for the preparation of polymers like (2) above, employs the use of highly toxic organotin reagents, which is undesirable for mass production.

Therefore, there is still a need for organic semiconducting (OSC) materials that are easy to synthesize, especially by methods suitable for mass production, show good structural organization and film-forming properties, exhibit good electronic properties, especially a high charge carrier mobility, good processability, especially a high solubility in organic solvents, and high stability in air. Especially for use in OPV cells, there is a need for OSC materials having a low bandgap, which enable improved light harvesting by the photoactive layer and can lead to higher cell efficiencies.

It was an aim of the present invention to provide compounds for use as organic semiconducting materials that do not have the drawbacks of prior art materials as described above, are easy to synthesize, especially by methods suitable for mass production, and do especially show good processability, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that these aims can be achieved by providing conjugated semiconducting polymers as described hereinafter. These polymers comprise an acceptor unit based on a group that is formed by introduction of two thiophene units onto a benzene core, to give 4,8-benzo[1,2-b;4,5-b']dithiophene (4,8-BDT), or derivatives or isomers thereof, which has additional solubilising groups R in 2- and 6-position:

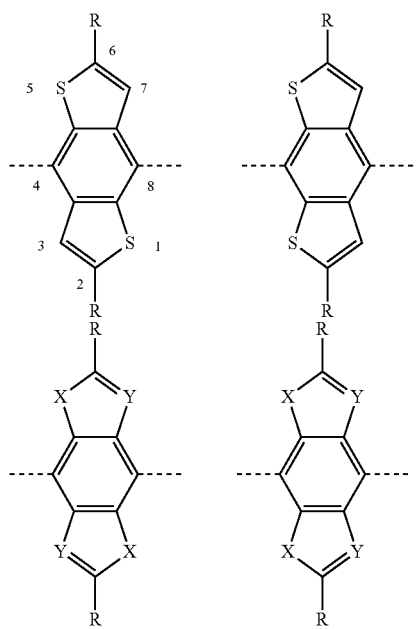

wherein X is S, Se or O, Y is CH, CR' or N', R is e.g. alkyl, alkylcarbonyl or alkyloxycarbonyl, and R' is e.g. alkyl.

When preparing polymers by aryl-aryl coupling of 4,8-BDT monomer units as used in the present invention, the coupling reaction occurs on the benzene ring of the BDT monomers, and not on the thiophene rings as in 2,6-BDT. This is expected to reduce or even avoid the above-mentioned problems observed in the Suzuki coupling of 2,6-BDT monomers. Also, the use of Stille coupling with highly toxic organotin agents can be avoided. The monomers and polymers of the present invention are therefore especially suitable for large scale production. At the same time, they show good processability, high solubility in organic solvents, a low bandgap and a high charge carrier mobility, and are thus promising materials for organic electronic OE devices, especially for OPV devices. M. Pomerantz, J. Wang, S. Seong, K. P. Starkey, L. Nguyen, D. S. Marynick, *Macromolecules,* 1994, 27, 7478-74853 reports a polymer of benzo[1,2-b:4,5-b']dithiophene-4,8-diylvinylene, which was prepared by a soluble precursor and then thermally converted as a thin film to an insoluble conjugated polymer. However, the final polymer was reported to be insoluble. Also, there was no reported indication that a substituted benzo[1,2-b:4,5-b']dithiophene unit would show promising performance in semiconducting polymers or be useful as an acceptor unit in copolymers for OPV use. Besides, there is no hint to prepare polymers by aryl-aryl coupling reactions of the monomeric units, or the potential problems linked to these reactions, or possible ways how to overcome these problems.

It was found that the polymers according to this invention are suitable for use as OSC materials in electronic devices, especially in OPV cells, as they have good processability and solubility, and at the same time show a high charge carrier mobility, a low bandgap and a high oxidative stability.

In particular it was found that the repeating units according to the present invention are suitable as acceptor units in dono-acceptor polymers, especially for use in bulk heterojunction (BHJ) OPV devices.

SUMMARY OF THE INVENTION

The invention relates to a conjugated polymer comprising one or more identical or different repeating units of formula I:

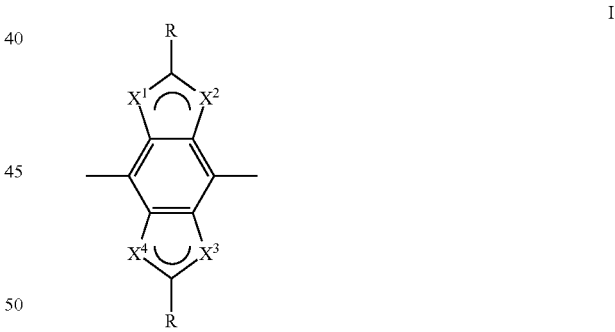

wherein
one of $X^1$ and $X^2$ is selected from S, Se and O, and the other is selected from CH, $CR^x$ and N,
one of $X^3$ and $X^4$ is selected from S, Se and O, and the other is selected from CH, $CR^x$ and N,
R on each occurrence identically or differently denotes straight-chain, branched or cyclic alkyl with 1 to 35 C atoms, in which one or more non-adjacent C atoms are optionally replaced by —O—, —S—, —CO—, —CO—O—, —O—CO—, —O—CO—O—, —$CR^0$=$CR^{00}$— or —C≡C— and in which one or more H atoms are optionally replaced by F, Cl, Br, I or CN, or denotes aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 2 to 40

C atoms that is unsubstituted or substituted by one or more non-aromatic groups $R^1$, $R^x$ is on each occurrence identically or differently straight-chain, branched or cyclic alkyl with 1 to 15 C atoms, in which one or more non-adjacent C atoms are optionally replaced by —O—, —S—, —CO—, —CO—O—, —O—CO—, O—CO—O—, —CR$^0$═CR$^{00}$— or —C≡C— and in which one or more H atoms are optionally replaced by F, Cl, Br, I or CN, $R^0$ and $R^{00}$ are independently of each other H or optionally substituted carbyl or hydrocarbyl optionally comprising one or more hetero atoms, $R^1$ is on each occurrence identically or differently H, halogen, —CN, —NC, —NCO, —NCS, —OCN, —SCN, —C(═O)NR$^0$R$^{00}$, —C(═O)X$^0$, —C(═O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable or crosslinkable group, Sp is a spacer group or a single bond, $X^0$ is halogen.

The invention further relates to a conjugated polymer of formula II

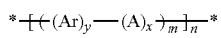

wherein

A is on each occurrence identically or differently a repeating unit of formula I as described above and below, Ar is, on each occurrence identically or differently, optionally substituted aryl or heteroaryl, $Y^1$ and $Y^2$ are independently of each other H, F, Cl or CN, m is on each occurrence identically or differently 1, 2 or 3, x is on each occurrence identically or differently 0 or 1, wherein in at least one sub-unit ((Ar)$_y$-(A)$_x$) x is 1, y is on each occurrence identically or differently 0 or 1, n is an integer >1.

The invention further relates to monomers containing a unit of formula I, which are suitable for the preparation of polymers as described above and below.

The invention further relates to a polymer blend comprising one or more polymers according to the present invention and one or more additional polymers, wherein these additional polymers are preferably selected from polymers having semiconducting, charge transport, hole/electron transport, hole/electron blocking, electrically conducting, photoconducting or light emitting properties.

The invention further relates to a formulation comprising one or more polymers or polymer blends according to the present invention and optionally one or more solvents, preferably selected from organic solvents.

The invention further relates to the use of polymers, polymer blends and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more polymers, polymer blends of formulations according to the present invention.

The invention further relates to an optical, electrooptical or electronic component or device comprising one or more polymers, polymer blends, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarizing layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

Figure 1:
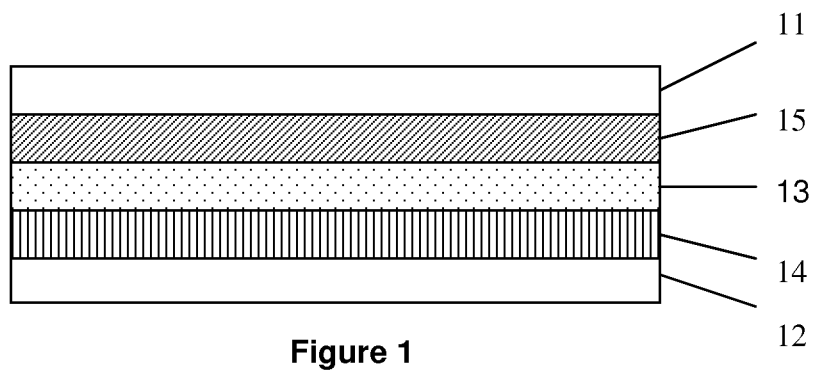
FIG. 1 exemplarily and schematically depicts a typical and preferred OPV device according to the present invention.

The monomers and polymers of the present invention are easy to synthesize and exhibit several advantageous properties, like a low bandgap, a high charge carrier mobility, a high solubility in organic solvents, a good processability for the device manufacture process, a high oxidative stability and a long lifetime in electronic devices.

In addition, they show the following advantageous properties:

i) The repeating units of formula I contain two five-membered thiophene rings that are fused to the central benzene ring which itself is contained within the backbone of the polymer. This increases the quinoidal contribution compared to an unsubstituted benzene and therefore lowers the band gap of the resultant polymer and results in improving the light harvesting ability of the material.

ii) Additional solubility can be introduced into the polymer by inclusion at the terminal thiophene positions of solubilising groups or co-monomers containing multiple solubilising groups The substituents in 2- and 6-position do thus increase the solubility of the polymer in common organic solvents, allowing the material to be easily solution processed.

iii) The unit of formula I is a good acceptor unit due to its high quinoidal contribution, which is ideal for the preparation of donor-acceptor polymer structures. These donor-acceptor polymer structures lead to low band gap polymers for OPV applications. Additional fine-tuning of the electronic energies (HOMO/LUMO levels) can be achieved by further modification of the benzo[1,2-b;4,5-b']dithiophene core and/or co-polymerisation with appropriate co-monomer(s), to afford promising materials for OPV applications.

iv) The units of formula I are planar structures that enable strong pi-pi stacking in the solid state leading to better charge transport properties in the form of higher charge carrier mobility.

v) The addition of reactive functionalities on the 4- and 8-position of the BDT units enables the preparation of regioregular homopolymers and copolymers, for example using Yamamoto, Suzuki or Stille coupling polymerization methods, which are known from the literature. The regioregular polymer has higher structural order in the solid state compared to regioirregular materials synthesized using a non-selective polymerization method. This leads to a polymer with a higher degree of intermolecular order and therefore higher charge carrier mobility in OFET and OPV devices.

vi) The positioning of reactive functionalities, such as a boronate, on the benzene ring at the 4- and 8-position in the BDT units enables the preparation of regioregular copolymers using Suzuki coupling methodology. Bis(boronate) monomers where the boronate functionality is sited on a benzene ring are liable to more hydrolytically and thermally stable than those where the boronate functionality is sited on a thiophene ring, which generally lead to low molecular weight polymers [see M. Jayakannan, J. L. J. van Dongen, R. A. J. Janssen, *Macromolecules*, 2001, 34, 5386]. This will therefore allow the preparation of higher molecular weight polymers, as required for OFET and OPV applications, using a non-toxic coupling methodology that avoids the use of highly toxic organotins reagents used in Stille coupling methodology.

vii) The polymers of the present invention have improved air stability, and show a higher open circuit potential ($V_{oc}$) in an OPV bulk-heterojunction device compared to a device containing poly(3-hexylthiophene) (P3HT).

viii) In the polymers of the present invention, the inclusion of additional electron-donating comonomers can yield a broad UV-Vis absorption spectrum with high absorption coefficient, thus leading to greater photon harvesting in an OPV bulk-heterojunction device.

The term "polymer" generally means a molecule of high relative molecular mass, the structure of which essentially comprises the multiple repetition of units derived, actually or conceptually, from molecules of low relative molecular mass (PAC, 1996, 68, 2291). The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having >1, preferably ≥5 repeating units, and an oligomer means a compound with >1 and <10, preferably <5, repeating units.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

The term "leaving group" means an atom or group (charged or uncharged) that becomes detached from an atom in what is considered to be the residual or main part of the molecule taking part in a specified reaction (see also PAC, 1994, 66, 1134).

The term "conjugated" means a compound containing mainly C atoms with sp²-hybridisation (or optionally also sp-hybridisation), which may also be replaced by hetero atoms. In the simplest case this is for example a compound with alternating C—C single and double (or triple) bonds, but does also include compounds with units like 1,3-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, trichloromethane is used as solvent. The degree of polymerization, also referred to as total number of repeating units, n, means the number average degree of polymerization given as $n=M_n/M_U$, wherein $M_n$ is the number average molecular weight and $M_U$ is the molecular weight of the single repeating unit, see J. M. G. Cowie, *Polymers: Chemistry & Physics of Modern Materials*, Blackie, Glasgow, 1991.

In the units of formula I, the group

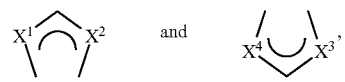

respectively,
denotes a group that forms a conjugated system together with the central benzene ring, and thus denotes

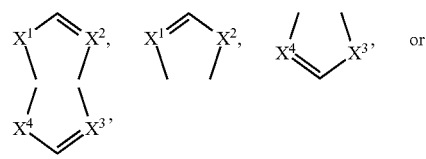

respectively.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, trichloromethane is used as solvent. The degree of polymerization (n) means the number average degree of polymerization given as $n=M_n/M_U$, wherein $M_U$ is the molecular weight of the single repeating unit as described in J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with up to 25 C atoms that may also comprise condensed rings and is optionally substituted with one or more groups L as defined above.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thieno-thiophene, dithienothiophene, fluorene and oxazole, all of which can be unsubstituted, mono- or polysubstituted with L as defined above. Very preferred rings are selected from pyrrole, preferably N-pyrrole, pyridine, preferably 2- or 3-pyridine, pyrimidine, thiophene preferably 2-thiophene, selenophene, preferably 2-selenophene, thieno[3,2-b]thiophene, thiazole, thiadiazole, oxazole and oxadiazole, especially preferably thiophene-2-yl, 5-substituted thiophene-2-yl or pyridine-3-yl, all of which can be unsubstituted, mono- or polysubstituted with L as defined above.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —CO—, these radicals are preferably neighbored. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

—$CY^1$=$CY^2$— is preferably —CH=CH—, —CF=CF— or —CH=C(CN)—.

Halogen is F, Cl, Br or I, preferably F, Cl or Br.

The polymers may also be substituted with a polymerisable or crosslinkable reactive group, which is optionally protected during the process of forming the polymer. Particular preferred polymers of this type are those of formula I wherein $R^1$ denotes P-Sp. These polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or crosslinkable group P is selected from $CH_2$=$CW^1$—CO—O—, $CH_2$=$CW^1$—CO—,

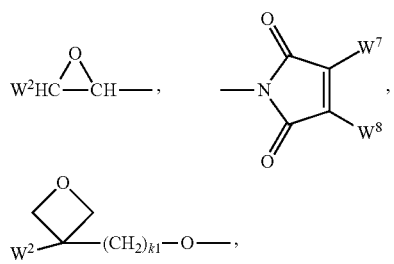

$CH_2$=$CW^2$—(O)$_{k1}$—, $CW^1$=CH—CO—(O)$_{k3}$—, $CW^1$=CH—CO—NH—, $CH_2$=$CW^1$—CO—NH—, $CH_3$—CH=CH—O—, $(CH_2$=CH)$_2$CH—OCO—, $(CH_2$=CH—$CH_2)_2$CH—O—CO—, $(CH_2$=CH)$_2$CH—O—, $(CH_2$=CH—$CH_2)_2$N—, $(CH_2$=CH—$CH_2)_2$N—CO—, HO—$CW^2W^3$—, HS—$CW^2W^3$—, H$W^2$N—, HO—$CW^2W^3$—NH—, $CH_2$=CH—(CO—O)$_{k1}$-Phe-(O)$_{k2}$—, $CH_2$=CH—(CO)$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, $k_1$, $k_2$ and $k_3$ being independently of each other 0 or 1, $k_3$ preferably being 1, and $k_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—CO—O—, $CH_2$=C($CH_3$)—CO—O—, $CH_2$=CF—CO—O—, $CH_2$=CH—O—, $(CH_2$=CH)$_2$CH—O—CO—, $(CH_2$=CH)$_2$CH—O—,

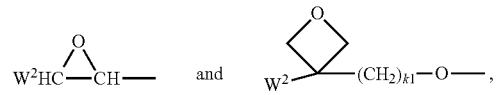

or protected derivatives thereof. Further preferred groups P are selected from the group consisting of vinyloxy, acrylate, methacrylate, fluoroacrylate, chloracrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, *Macromol. Chem*, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—OCO—, —CO—$NR^0$—, —$NR^0$—CO—, —$NR^0$—CO—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—COO—, —OCO—CH=CH— or a single bond, $R^0$ and $R^{00}$ are independently of each other H or alkyl with 1 to 12 C-atoms, and $Y^1$ and $Y^2$ are independently of each other H, F, Cl or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C— or a single bond, in particular —O—, —S—, —C≡C—, —CY$^1$=CY$^2$— or a single bond. In another preferred embodiment X' is a group that is able to form a conjugated system, such as —C≡C— or —CY$^1$=CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The units of formula I are preferably selected from the following formulae:

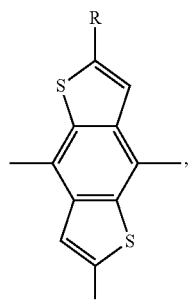

A

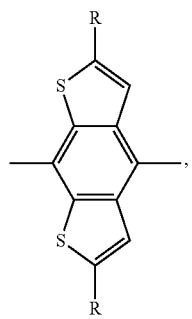

B

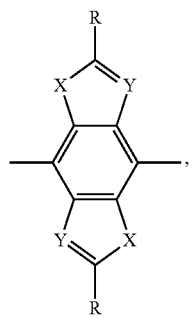

C

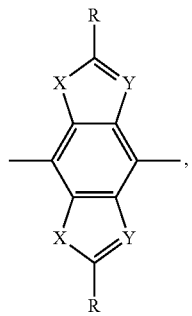

D wherein X is S, Se or O, and Y is CH, CR$^x$ or N, and R and R$^x$ have independently of each other one of the meanings given in formula I or one of the preferred meanings as given above and below.

The polymers containing units of formula I, especially those of formula II, are preferably selected of formula IIa

IIa wherein A, Ar, m, n, x and y have the meanings of formula I and II, and
R$^2$ and R$^3$ have independently of each other one of the meanings of R$^1$, preferably halogen, or denote H, —CH$_2$Cl, —CHO, —CH=CH$_2$, —SiR'R"R''', —Sn-R'R"R''', —BR'R", —B(OR')(OR"), —B(OH)$_2$, or P-Sp, wherein P and Sp are as defined in formula I, and R', R" and R''' have independently of each other one of the meanings of R$^0$ given in formula I, and R' and R" may also form a ring together with the hetero atom to which they are attached.

In the polymers according to the present invention, the total number of repeating units n is preferably ≥5, very preferably ≥10, most preferably 50, and preferably up to 500, very preferably up to 1,000, most preferably up to 2,000, including any combination of the aforementioned lower and upper limits of n.

The polymers of the present invention include homopolymers and copolymers, like statistical or random copolymers, alternating copolymers and block copolymers, as well as combinations thereof.

Block copolymers may for example comprise or consist of one or more blocks formed by units of formula I and one or more blocks formed by units Ar, wherein Ar has one of the meanings as described above and below.

Another aspect of the invention relates to monomers of formula Ia

Ia wherein A is a unit of formula I or selected from its preferred subformulae or preferred meanings as described above and below, and R$^2$ and R$^3$ have the meanings given in formula IIa.

Especially preferred are monomers of formula Ia wherein R$^2$ and R$^3$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH and —Sn(Z$^4$)$_3$, wherein Z$^{1-4}$ are selected from the group consisting of alkyl and aryl, each being optionally substituted, and two groups $Z^2$ may also form a cyclic group.

Preferably the repeating units of formula I, and the monomers of formula Ia and polymers of formula II and IIa containing them, are selected from the following list of preferred embodiments:

$X^1$ and $X^3$ are selected from S, Se and O, and $X^2$ and $X^4$ are selected from CH, $CR^x$ and N, $X^2$ and $X^3$ are selected from S, Se and O, and $X^1$ and $X^4$ are selected from CH, $CR^x$ and N, the groups of $X^{1-4}$ selected from S, Se and O denote S, the groups of $X^{1-4}$ selected from S, Se and O denote Se, the groups of $X^{1-4}$ selected from S, Se and O denote 0, the groups of $X^{1-4}$ selected from CH, $CR^x$ and N denote CH, the groups of $X^{1-4}$ selected from CH, $CR^x$ and N denote $CR^x$, the groups of $X^{1-4}$ selected from CH, $CR^x$ and N denote N, $X^1$ and $X^3$ denote S, and $X^2$ and $X^4$ denote CH, $X^1$ and $X^4$ denote S, and $X^2$ and $X^3$ denote CH, m is 1 and y is 0, thereby forming a repeating unit [A], m is 1 and y is 1, thereby forming a repeating unit [Ar-A], m is 2, and in one sub-unit $((Ar)_y-(A)_x)$ y is 0 and in the other unit y is 1, thereby forming a repeating unit [A-Ar-A] or [Ar-A-A], m is 2, and in one sub-unit $((Ar)_y-(A)_x)$ x is 0 and in the other unit x is 1, thereby forming a repeating unit [Ar—Ar-A] or [Ar-A-Ar], Ar is an aryl or heteroaryl group which has electron donor properties, including but not limited to aryl and heteroaryl groups selected from the group consisting of selenophene-2,5-diyl, thiophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, 2,2-dithiophene, 2,2-diselenophene, dithieno[3,2-b:2',3'-d]silole-5,5-diyl, 4H-cyclopenta[2,1-b:3,4-b']dithiophene-2,6-diyl, 2,7-di-thien-2-yl-carbazole, 2,7-di-thien-2-yl-fluorene, indaceno[1,2-b:5,6-b']dithiophene-2,7-diyl, benzo[1",2":4,5;4"',5"':4',5]bis(silolo[3,2-b:3',2'-b]thiophene)-2,7-diyl, 2,7-di-thien-2-yl-indaceno[1,2-b:5,6-b']dithiophene, 2,7-di-thien-2-yl-benzo[1",2":4,5;4"',5"':4',5]bis(silolo[3,2-b:3',2'-b]thiophene)-2,7-diyl, 2,7-di-thien-2-yl-phenanthro[1,10,9,8-c,d,e,f,g]carbazole, all of which are unsubstituted, or mono- or polysubstituted, preferably with R, $R^1$ or $R^y$ as defined above and below, Ar is an aryl or heteroaryl group which has electron acceptor properties, including but not limited to aryl and heteroaryl groups selected from the group consisting of 4,7-di-thien-2-yl-benzo[1,2,3]thiadiazole, 4,7-di-thien-2-yl-benzo[1,2,3]selenadiazole, 3,4-difluoro-thiophene-2,5-diyl, 2,5-di-thien-2-yl-thieno[3,4-b]pyrazine, 5,8-di-thien-2-yl-quinoxaline, thieno[3,4-b]thiophene-4,6-diyl, 4,6-di-thien-2-yl-thieno[3,4-b]thiophene, thieno[3,4-b]thiophene-6,4-diyl, 6,4-di-thien-2-yl-thieno[3,4-b]thiophene, 3,6-di-thien-2-yl-pyrrolo[3,4-c]pyrrole-1,4-dione, all of which are unsubstituted, or mono- or polysubstituted, preferably with R, $R^1$ or $R^y$ as defined above and below, Ar is optionally substituted by one or more groups R, $R^1$ or $R^y$ as described above and below, Ar is selected from aryl or heteroaryl, preferably selected, on each occurrence identically or differently, from the group consisting of selenophene-2,5-diyl, thiophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, 2,2-dithiophene, 2,2-diselenophene, dithieno[3,2-b:2',3'-d]silole-5,5-diyl, 4H-cyclopenta[2,1-b:3,4-b']dithiophene-2,6-diyl, 2,7-di-thien-2-yl-carbazole, 2,7-di-thien-2-yl-fluorene, indaceno[1,2-b:5,6-b']dithiophene-2,7-diyl, benzo[1",2":4,5;4"',5"':4',5]bis(silolo[3,2-b:3',2'-b]thiophene)-2,7-diyl, 2,7-di-thien-2-yl-indaceno[1,2-b:5,6-b']dithiophene, 2,7-di-thien-2-yl-benzo[1",2":4,5;4"',5"':4',5]bis(silolo[3,2-b:3',2'-b]thiophene)-2,7-diyl, 2,7-di-thien-2-yl-phenanthro[1,10,9,8-c,d,e,f,g]carbazole, 4,7-di-thien-2-yl-benzo[1,2,3]thiadiazole, 4,7-di-thien-2-yl-benzo[1,2,3]selenadiazole, 3,4-difluorothiophene-2,5-diyl, 2,5-di-thien-2-yl-thieno[3,4-b]pyrazine, 5,8-di-thien-2-yl-quinoxaline, thieno[3,4-b]thiophene-4,6-diyl, 4,6-di-thien-2-yl-thieno[3,4-b]thiophene, thieno[3,4-b]thiophene-6,4-diyl, 6,4-di-thien-2-yl-thieno[3,4-b]thiophene, 3,6-di-thien-2-yl-pyrrolo[3,4-c]pyrrole-1,4-dione, all of which are unsubstituted, or mono- or polysubstituted, preferably with R, $R^1$ or $R^y$ as defined above and below, n is at least 5, preferably at least 10, very preferably at least 50, and up to 2,000, preferably up to 500.

Mw is at least 5,000, preferably at least 8,000, very preferably at least 10,000, and preferably up to 300,000, very preferably up to 100,000, R is primary alkyl with 1 to 30 C atoms, secondary alkyl with 3 to 30 C atoms, or tertiary alkyl with 4 to 30 C atoms, wherein in all these groups one or more H atoms are optionally replaced by F, R is aryl, alkylated aryl or alkoxy aryl with 4 to 40 C atoms, R is —CO—$R^y$, —CO—O—$R^y$, or —O—CO—$R^y$, very preferably —CO—$R^y$ or —CO—O—$R^y$, wherein $R^y$ is straight-chain, branched or cyclic alkyl with 1 to 30 C atoms, in which one or more non-adjacent C atoms are optionally replaced by —O—, —S—, —CO—, —CO—O—, —O—CO—, —O—CO—O—, —$CR^0$=$CR^{00}$— or —C≡C— and in which one or more H atoms are optionally replaced by F, Cl, Br, I or CN, or $R^y$ is aryl or heteroaryl having 2 to 30 C atoms that is unsubstituted or substituted by one or more non-aromatic groups $R^1$ as defined in formula I, $R^y$ is primary alkyl with 1 to 30 C atoms, very preferably with 1 to 15 C atoms, secondary alkyl with 3 to 30 C atoms, or tertiary alkyl with 4 to 30 C atoms, wherein in all these groups one or more H atoms are optionally replaced by F, $R^y$ is —$(CH_2)_o$—$CR^aR^bR^c$, wherein o is 0, 1, 2, 3, 4 or 5, very preferably 0, 1 or 2, and $R^a$, $R^b$ and $R^c$ are independently of each other $C_1$-$C_{12}$-alkyl, very preferably $C_1$-$C_8$-alkyl, which is optionally substituted by one or more F atoms, and wherein optionally one of $R^a$, $R^b$ and $R^c$ is H, $R^y$ is aryl or alkylated aryl with 4 to 30 C atoms, $R^x$ is alkyl with 1 to 15 C atoms, $R^0$ and $R^{00}$ are selected from H or $C_1$-$C_{10}$-alkyl, $R^2$ and $R^3$ are selected from H, halogen, —$CH_2Cl$, —CHO, —CH=$CH_2$, —SiR'R"R"', —SnR'R"R"', —BR'R", —B(OR')(OR"), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, $R^2$ and $R^3$ are, preferably independently of each other, selected from the group consisting of Cl, Br, I, O-tosylate, O-triflate, O-mesylate, 0-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, very preferably from Br, R is P-Sp-.

Preferred polymers of formula II are selected from the following formulae:

II1

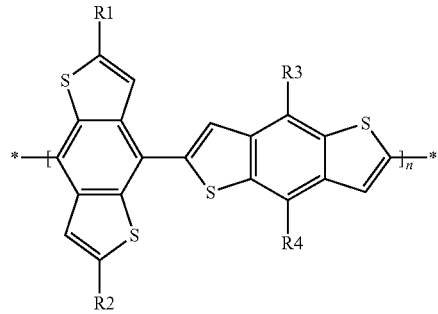

II5

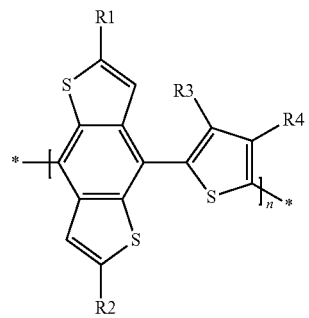

II6

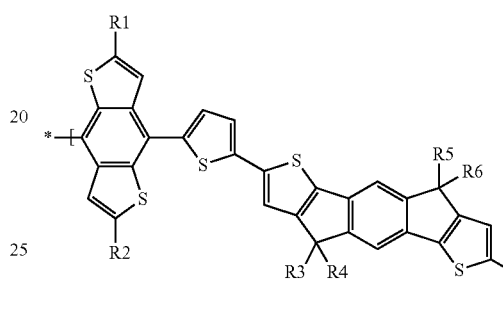

II2

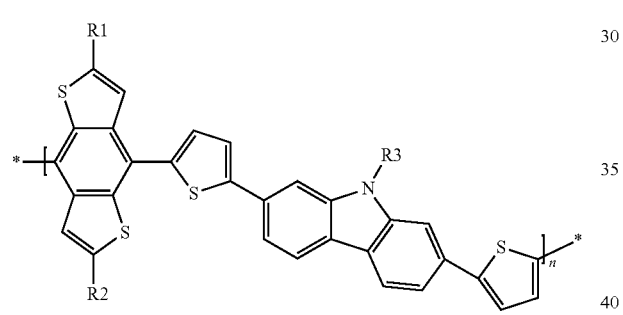

II7

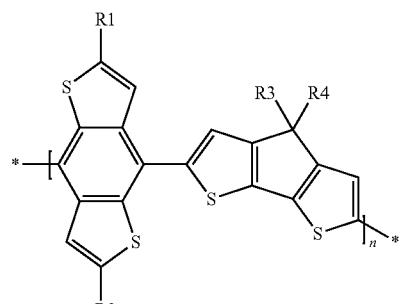

II3

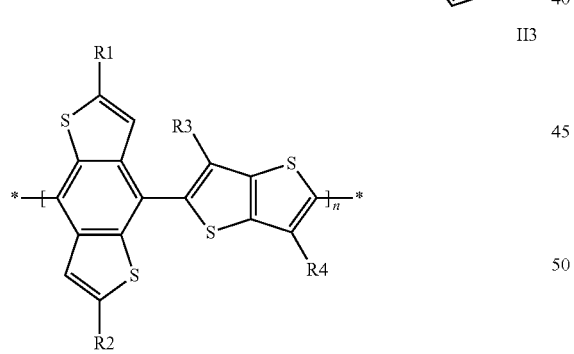

II8

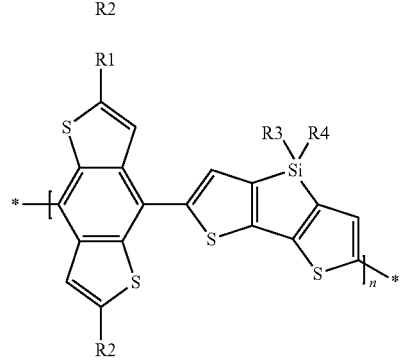

II4

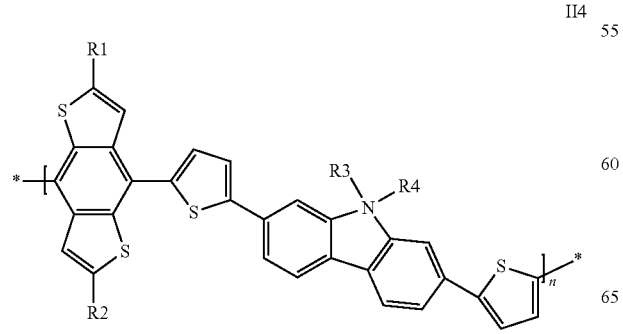

II9

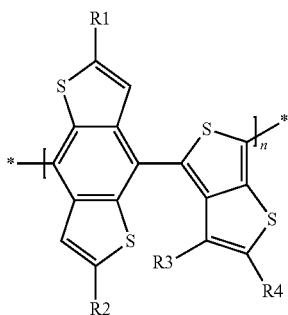

II10

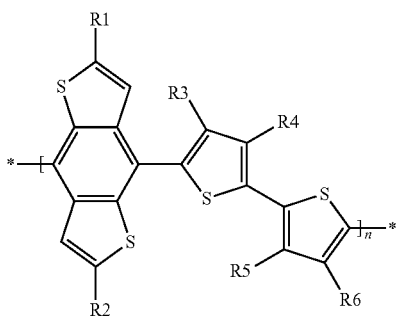

II11 wherein R1, R2, R3, R4, R5 and R6 have independently of each other one of the meanings of R as given in formula I or selected from the preferred meanings of R as described above and below; preferably wherein R1 and R2 independently of each other denote —CO—$R^y$ or —COO—$R^y$ with $R^y$ being as described above and R3, R4, R5 and R6 independently of each other denote H or R.

Very preferred polymers of formula IIa are selected of the formula $R^2$-chain-$R^3$ wherein "chain" is a polymer chain selected from formulae II1-II11, and $R^2$ and $R^3$ have one of the meanings of $R^2$ and $R^3$ given in formula IIa or one of the preferred meanings of $R^2$ and $R^3$ given above and below.

The polymers of the present invention can be synthesized according to or in analogy to methods that are known to the skilled person and are described in the literature. Other methods of preparation can be taken from the examples. For example, they can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The monomers which are polymerised to form the repeat units of the polymers can be prepared according to methods which are known to the person skilled in the art.

Preferably the polymers are prepared from monomers of formula Ia or its preferred embodiments as described above and below.

Another aspect of the invention is a process for preparing a polymer by coupling one or more identical or different monomeric units of formula I or monomers of formula Ia with each other and/or with one or more comonomers in a polymerisation reaction, preferably in an aryl-aryl coupling reaction.

Suitable and preferred comonomers are those of the formula $R^2$—Ar—$R^3$ wherein Ar, $R^2$ and $R^3$ are as defined above.

Preferred methods for polymerisation are those leading to C—C-coupling or C—N-coupling, like Suzuki polymerisation, as described for example in WO 00/53656, Yamamoto polymerisation, as described in for example in T. Yamamoto et al., Progress in Polymer Science 1993, 17, 1153-1205 or in WO 2004/022626 A1, and Stille coupling. For example, when synthesizing a linear polymer by Yamamoto polymerisation, monomers as described above having two reactive halide groups $R^2$ and $R^3$ is preferably used. When synthesizing a linear polymer by Suzuki polymerisation, preferably a monomer as described above is used wherein at least one reactive group $R^2$ or $R^3$ is a boronic acid or boronic acid derivative group.

Suzuki polymerisation may be used to prepare homopolymers as well as statistical, alternating and block random copolymers. Statistical or block copolymers can be prepared for example from the above monomers of formula Ia wherein one of the reactive groups $R^2$ and $R^3$ is halogen and the other reactive group is a boronic acid or boronic acid derivative group. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol)$_4$. Preferred Pd(II) salts include palladium acetate, i.e. Pd(OAc)$_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O—SO$_2$Z$^1$ can be used wherein Z$^1$ is as described above. Particular examples of such leaving groups are tosylate, mesylate and triflate.

Especially suitable and preferred synthesis methods of the repeating units and monomers of formula I and Ia, and their homo- and co-polymers of formula II and IIa, are illustrated in the synthesis schemes shown hereinafter. Therein R is as defined in formula I.

A suitable synthesis method for the preparation of 4,8-dibromo-benzo[1,2-b;4,5-b']dithiophene-2,6-dicarboxylic acid bis-(alkyl) ester is exemplarily shown in Scheme 1.

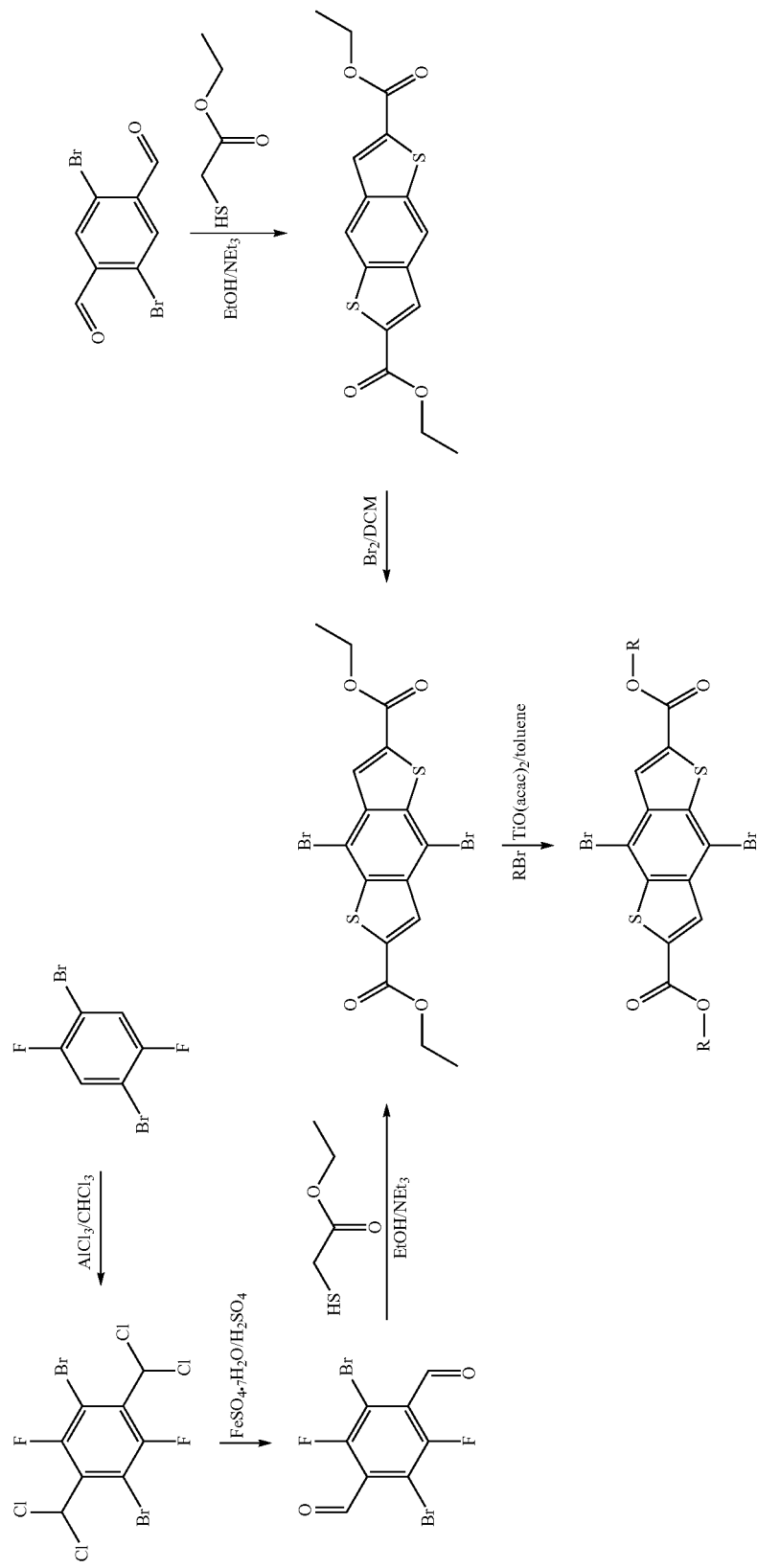

A suitable method for further functionalisation of 4,8-dibromo-benzo[1,2-b;4,5-b']dithiophene is exemplarily shown in Scheme 2.

Scheme 2-Synthesis of 4,8-functionalised-benzo[1,2-b;4,5-b']dithiophene

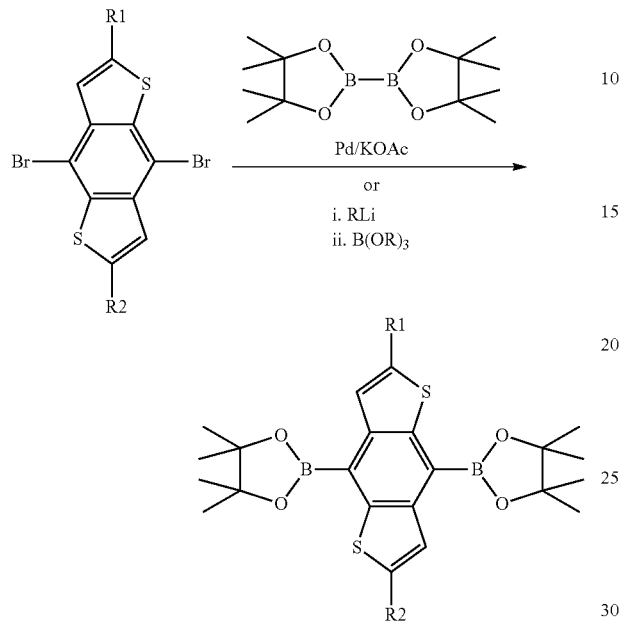

Scheme 4-Synthesis of alternating co-polymers of 4,8-benzo[1,2-b;4,5-b']dithiophenes

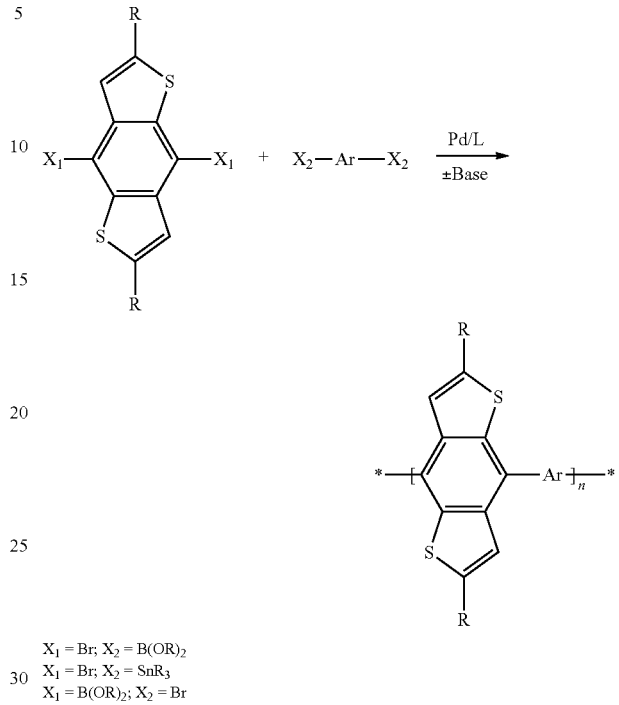

$X_1 = Br; X_2 = B(OR)_2$
$X_1 = Br; X_2 = SnR_3$
$X_1 = B(OR)_2; X_2 = Br$

The polymers can be synthesized by various organometallic catalyzed reaction such as Yamamoto coupling (see e.g. Yamamoto, T.; Morita, A.; Miyazaki, Y.; Maruyama, T.; Wakayama, H.; Zhou, Z. H.; Nakamura, Y.; Kanbara, T.; Sasaki, S.; Kubota, K. *Macromolecules* 1992, 25, 1214-1223, and Yamamoto, T.; Takimiya, K. *J. Am. Chem. Soc.* 2007, 129, 2224-2225), Suzuki coupling (see e.g. Schlüter, A. D. *J. Polym. Sci., Part A: Polym. Chem.* 2001, 39, 1533-1556), or Stille coupling (see e.g. Bao, Z.; Chan, W. K.; Yu, L. *J. Am. Chem. Soc.* 1995, 117, 12426-12435). The homopolymers are preferably synthesized using Yamamoto or Suzuki coupling, as illustrated in the Schemes below.

Suitable methods for the homopolymerisation and copolymerisation of 4,8-dibromo-benzo[1,2-b;4,5-b']dithiophene are shown in Schemes 3, 4 and 5 below, where R, Ar and n are as defined in formula I and II, Ar' has one of the meanings of Ar, and a, b, c and d are 0 or 1.

Scheme 5-Synthesis of random co-polymers of 4,8-benzo[1,2-b;4,5-b']dithiophenes

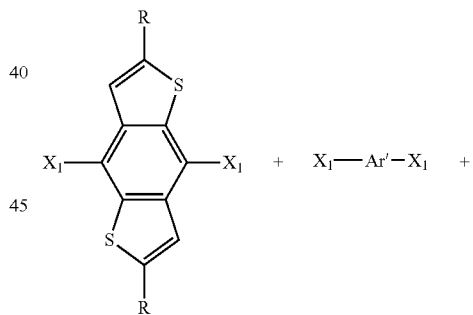

Scheme 3-Synthesis of homopolymers of 4,8-benzo[1,2-b;4,5-b']dithiophenes

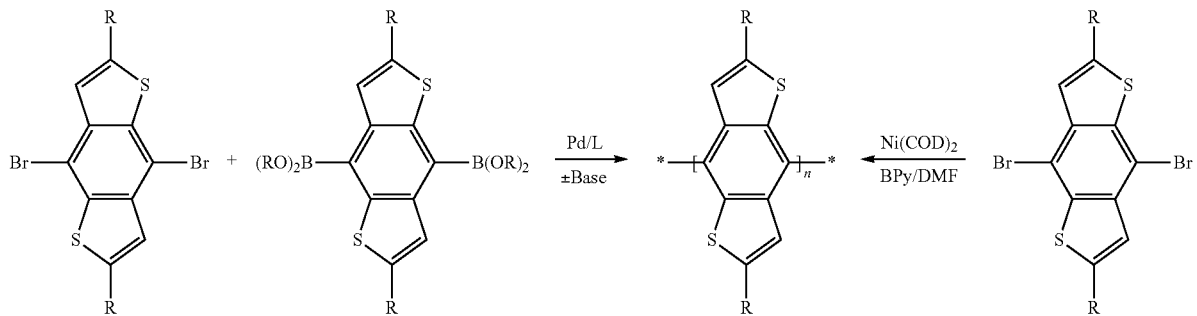

-continued

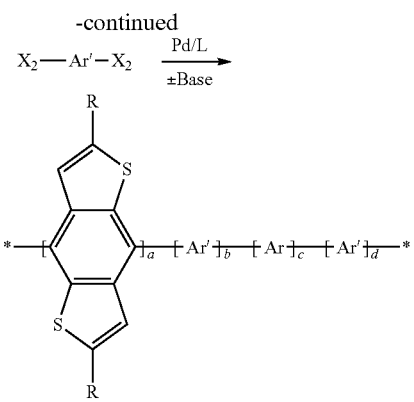

$X_1 = Br; X_2 = B(OR)_2$
$X_1 = Br; X_2 = SnR_3$
$X_1 = B(OR)_2; X_2 = Br$

The novel methods of preparing monomers and polymers as described above and below are another aspect of the invention.

The polymers according to the present invention can also be used in polymer blends, for example together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers or formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers according to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting polymer, polymer blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarizing layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or an structural analogous compound with e.g. a $C_{70}$ fullerene group ($C_{70}$PCBM), or a polymer (see for example Coakley, K. M. and McGehee, M. D. *Chem. Mater.* 2004, 16, 4533).

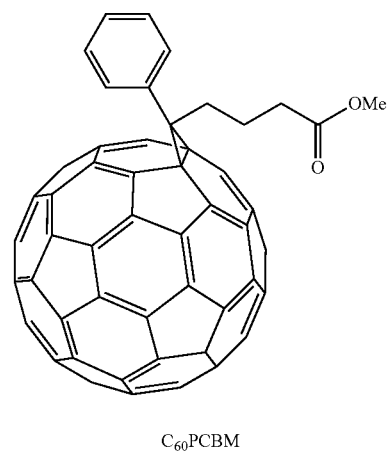 [SMILES: COC(=O)CCCC1(c2ccccc2)C23C=C4CC5=CC6C=C7Cc8cc9cc%10c%11c(c%12c%13c%14c(c4c5c4c%14c5c(c7c8c7c9c%11c%13c57)C46)C%1221)C(=C3)C%10]

$C_{60}$PCBM

A preferred material of this type is a blend or mixture of a polymer according to the present invention with a $C_{60}$ or $C_{70}$ fullerene or modified fullerene like PCBM. Preferably the ratio polymer:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently OPV device performance.

The OPV device can for example be of any type known from the literature [see e.g. Waldauf et al., Appl. Phys. Lett. 89, 233517 (2006)].

FIG. 1 exemplarily and schematically depicts a typical and preferred OPV device according to the present invention, comprising:
- a low work function electrode (11) (for example a metal, such as aluminum), and a high work function electrode (12) (for example ITO), one of which is transparent,
- a layer (13) (also referred to as "active layer") comprising a hole transporting material and an electron transporting material, preferably selected from OSC materials, situated between the electrodes (11,12); the active layer can exist for example as a bilayer or two distinct layers or blend or mixture of p-type and n-type semiconductor, forming a bulk heterjunction (BHJ) (see for example Coakley, K. M. and McGehee, M. D. Chem. Mater. 2004, 16, 4533),
- an optional conducting polymer layer (14), for example comprising a blend of PEDOT:PSS (poly(3,4-ethylenedioxythiophene): poly(styrenesulfonate)), situated between the active layer (13) and the high work function electrode (12), to modify the work function of the high work function electrode to provide an ohmic contact for holes,
- an optional coating (15) (for example of LiF) on the side of the low workfunction electrode (11) facing the active layer (13), to provide an ohmic contact for electrons.

Figure 2:
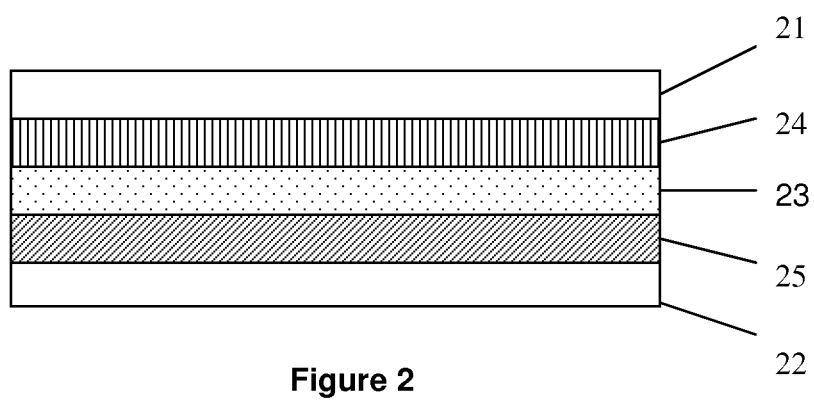
FIG. 2 exemplarily and schematically depicts a typical and preferred inverted OPV device according to the present invention.

FIG. 2 exemplarily and schematically depicts a typical and preferred inverted OPV device according to the present invention, comprising:
- a low work function electrode (21) (for example a metal, such as gold), and a high work function electrode (22) (for example ITO), one of which is transparent,
- a layer (23) (also referred to as "active layer") comprising a hole transporting material and an electron transporting material, preferably selected from OSC materials, situated between the electrodes (21,22); the active layer can exist for example as a bilayer or two distinct layers or blend or mixture of p-type and n-type semiconductor, forming a BHJ,
- an optional conducting polymer layer (24), for example comprising a blend of PEDOT:PSS, situated between the active layer (23) and the low work function electrode (21) to provide an ohmic contact for electrons,
- an optional coating (25) (for example of $TiO_x$) on the side of the high workfunction electrode (22) facing the active layer (23), to provide an ohmic contact for holes.

In the OPV devices of the present invent invention as exemplarily depicted in FIGS. 1 and 2, the p-type and n-type semiconductor materials are preferably selected from the materials, like the polymer/fullerene systems, as described above. If the bilayer is a blend an optional annealing step may be necessary to optimize device performance.

The compound, formulation and layer of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processability of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
- a source electrode,
- a drain electrode,
- a gate electrode,
- a semiconducting layer,
- one or more gate insulator layers,
- optionally a substrate.

wherein the semiconductor layer preferably comprises a polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377).

Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to the present invention, especially those which show photoluminescent properties, may be employed as materials of light sources, e.g., of display devices such as described in EP 0 889 350 A1 or by C. Weder et al., Science, 279, 1998, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_{3-}$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)$ $(SbCl_6^-)$, $(NO_2^+)(BF_4^-)$, $AgClO_4$, $H_2IrCl_6$, $La(NO_3)_3\cdot6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarizing layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., Nature Photonics 2008 (published online Sep. 28, 2008).

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention.

Independent protection may be sought for these features in addition to or alternative to any invention presently claimed.

The invention will now be described in more detail by reference to the following examples, which are illustrative only and do not limit the scope of the invention.

Example 1

1,4-Dibromo-2,5-bis-dichloromethyl-3,6-difluoro-benzene

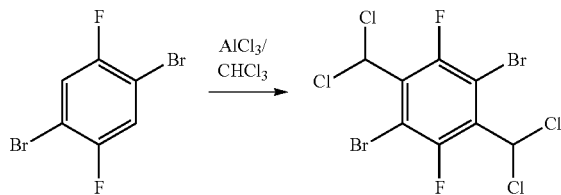 [SMILES: Fc1cc(Br)c(F)cc1Br ; Fc1c(Br)c(C(Cl)Cl)c(F)c(Br)c1C(Cl)Cl]

To a stirred solution of 1,4-dibromo-2,5-difluorobenzene (10 g, 37 mmol) in anhydrous chloroform (300 cm$^3$) under nitrogen is added anhydrous aluminium chloride (25 g, 190 mmol). The mixture is then heated at reflux for 113 hours. The mixture allowed to cool and poured onto ice (500 cm$^3$) and the product extracted with dichloromethane (3×300 cm$^3$). The combined organic extracts dried over anhydrous magnesium sulfate, filtered and the solvent removed in vacuo. The crude is purified by column chromatography (40-60 petroleum ether) to give 1,4-dibromo-2,5-bis-dichloromethyl-3,6-difluoro-benzene as a pale yellow solid (2.68 g, 16%). $^1$H NMR (300 MHz, CDCl$_3$) 7.18 (2H, d, CH, J 2.3).

2,5-Dibromo-3,6-difluoro-benzene-1,4-dicarbaldehyde

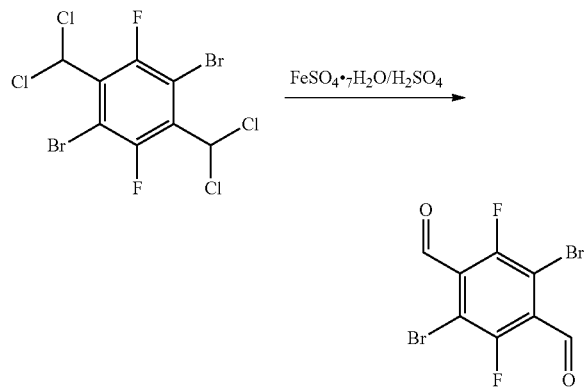

A solution of 1,4-dibromo-2,5-bis-dichloromethyl-3,6-difluoro-benzene (2.68 g, 6.1 mmol), 98-100% sulfuric acid (50 cm$^3$) and iron (II) sulfate heptahydrate (0.34 g, 1.2 mmol) is heated under nitrogen at 150° C. for 2 hours. The mixture allowed to cool to 23° C. and poured onto ice (3000 cm$^3$) and the product extracted with dichloromethane (3×600 cm$^3$). The combined organic extracts dried over anhydrous magnesium sulfate, filtered through a plug of silica (dichloromethane) and the solvent removed in vacuo. The crude recrystallised from 80-100 petroleum ether/dichloromethane to give 2,5-dibromo-3,6-difluoro-benzene-1,4-dicarbaldehyde as light brown crystals (12.59 g, 59%). $^1$H NMR (300 MHz, CDCl$_3$) 10.31 (2H, s, CHO).

Benzo[1,2-b;4,5-b']dithiophene-2,6-dicarboxylic acid diethyl ester

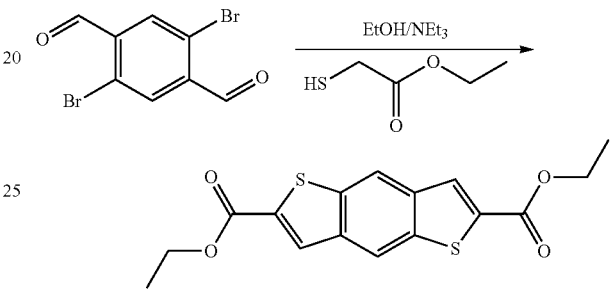

Ethyl thioglycolate (1.55 cm$^3$, 13.7 mmol) is added to a stirred mixture of 2,5-dibromo-benzene-1,4-dicarbaldehyde (2.0 g, 6.9 mmol), triethylamine (1.9 cm$^3$, 13.7 mmol) and ethanol (20 cm$^3$). The mixture is then heated at reflux for 17 hours. Further ethyl thioglycolate (0.8 cm$^3$) and triethylamine (0.95 cm$^3$) is added to the mixture and the mixture heated at reflux for 24 hours. The mixture allowed to cool and poured into water (100 cm$^3$). The precipitate is collected by filtration and washed with water (50 cm$^3$) and methanol (30 cm$^3$). The crude is purified by recrystallisation from 1,4-dioxane to give benzo[1,2-b;4,5-b']dithiophene-2,6-dicarboxylic acid diethyl ester as an off white solid, (0.05 g, 2%). MS (m/e): 334 (M$^+$, 100%), 306, 289, 278, 261, 233, 189.

4,8-Dibromo-benzo[1,2-b;4,5-b']dithiophene-2,6-dicarboxylic acid diethyl ester

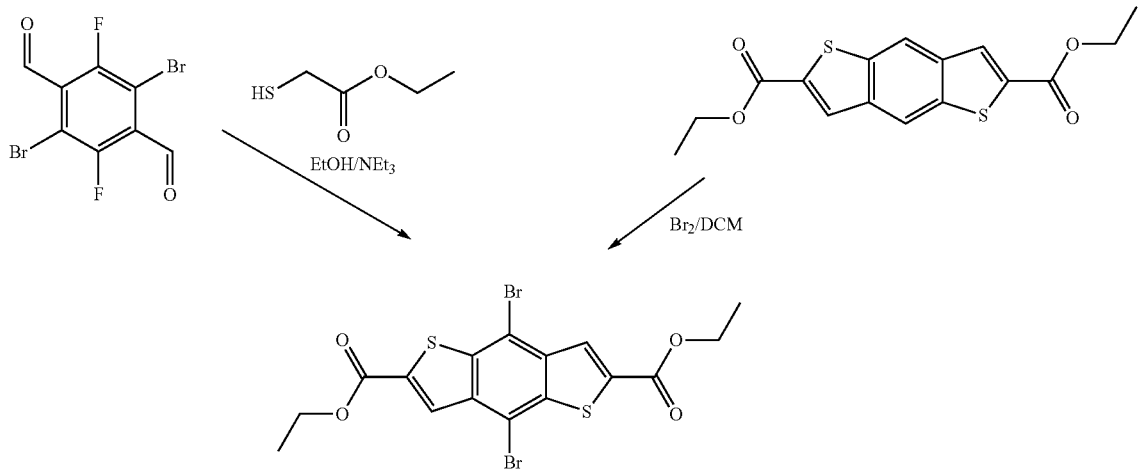

Ethyl thioglycolate (0.34 cm³, 3.0 mmol) is added to a stirred mixture of 2,5-dibromo-3,6-difluoro-benzene-1,4-dicarbaldehyde (0.50 g, 1.5 mmol), triethylamine (0.43 cm³, 3.0 mmol) and ethanol (15 cm³). The mixture is then heated at reflux for 2 hours. The mixture allowed to cool and poured into water (50 cm³). The precipitate is collected by filtration and washed with water (2×50 cm³) and methanol (50 cm³). The crude is purified by recrystallisation from N,N-dimethylformamide to give 4,8-dibromo-benzo[1,2-b;4,5-b']dithiophene-2,6-dicarboxylic acid diethyl ester as a yellow solid (0.25 g, 33%). ¹H NMR (300 MHz, CDCl₃) 1.46 (6H, t, CH₃, J 7.2), 4.46 (4H, q, CH₂, J 7.2), 8.28 (2H, s, ArH).

Example 2

A mixture of benzo[1,2-b;4,5-b']dithiophene-2,6-dicarboxylic acid diethyl ester (520 mg, 1.6 mmol), dichloromethane (50 cm³) and bromine (0.16 cm³, 3 mmol) is stirred at 23° C. for 5 days. Further bromine (0.03 cm³) is added and the mixture stirred at 23° C. for 41 hours. Aqueous sodium sulfate (10 cm³) is added and the mixture stirred for 20 minutes. Water (40 cm³) and methanol (100 cm³) is added and the mixture cooled over ice. The precipitate collected by filtration and washed with methanol (20 cm³). The crude is recrystallised from N,N-dimethylformamide to give 4,8-dibromo-benzo[1,2-b;4,5-b']dithiophene-2,6-dicarboxylic acid diethyl ester as a yellow solid (0.10 g, 13%).

4,8-Dibromo-benzo[1,2-b;4,5-b']dithiophene-2,6-dicarboxylic acid bis-(2-ethyl-hexyl) ester

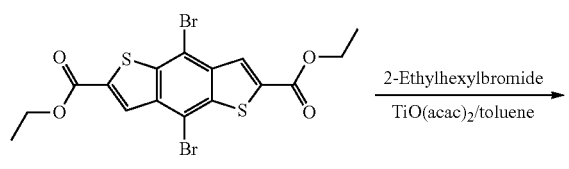

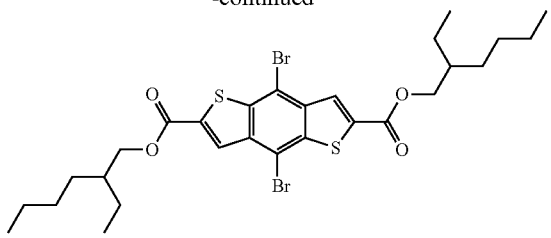

Titanium (IV) oxide bis(2,4-pentanedionate) (2 mg, 0.008 mmol) is added to a suspension of 4,8-dibromo-benzo[1,2-b;4,5-b']dithiophene-2,6-dicarboxylic acid diethyl ester (320 mg, 0.65 mmol) and 2-ethylhexanol (0.20 cm3, 1.3 mmol) in anhydrous toluene (25 cm³). The mixture was then heated at reflux for 17 hours under Dean-Stark conditions (1 cm³) of water was added to the Dean-Stark trap to help removal of the ethanol generated. Further titanium (IV) oxide bis(2,4-pentanedionate) (20 mg) and 2-ethylhexanol (1.0 cm³, 6.5 mmol) was added and the mixture heated at reflux for a further 17 hours. The reaction mixture allowed to cool and poured into water (50 cm³). The product extracted with dichloromethane (2×50 cm³) and the combined organics dried over anhydrous magnesium sulfate, filtered and the solvent removed in vacuo. The crude was purified by column chromatography (SP1, 100 g cartridge, petrol to DCM) to give 4,8-dibromo-benzo[1,2-b;4,5-b']dithiophene-2,6-dicarboxylic acid bis-(2-ethyl-hexyl) ester as a yellow solid (0.41 g, 96%). ¹H NMR (300 MHz, CDCl₃) 0.89-1.02 (12H, m, CH₃), 1.30-1.55 (16H, m, CH₂), 1.70-1.84 (2H, m, CH), 4.32 (4H, d, ArCH₂, J 5.8), 8.23 (2H, s, ArH); ¹³C NMR (300 MHz, CDCl₃) 11.1, 14.1, 23.0, 23.9, 29.0, 30.5, 38.9, 68.6, 111.4, 129.8, 136.9, 137.7, 141.1, 162.0.

Poly{4,7-5,6-bis-octyloxy-benzo[1,2,5]thiadiazole}-co-{2,5-thienyl}-co-{4,8-benzo[1,2-b;4,5-b']dithiophene-2,6-dicarboxylic acid bis-(2-ethyl-hexyl) ester} (1)

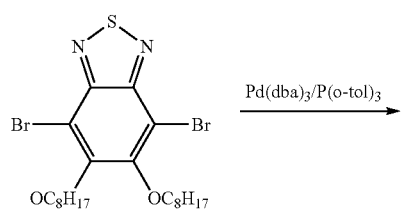

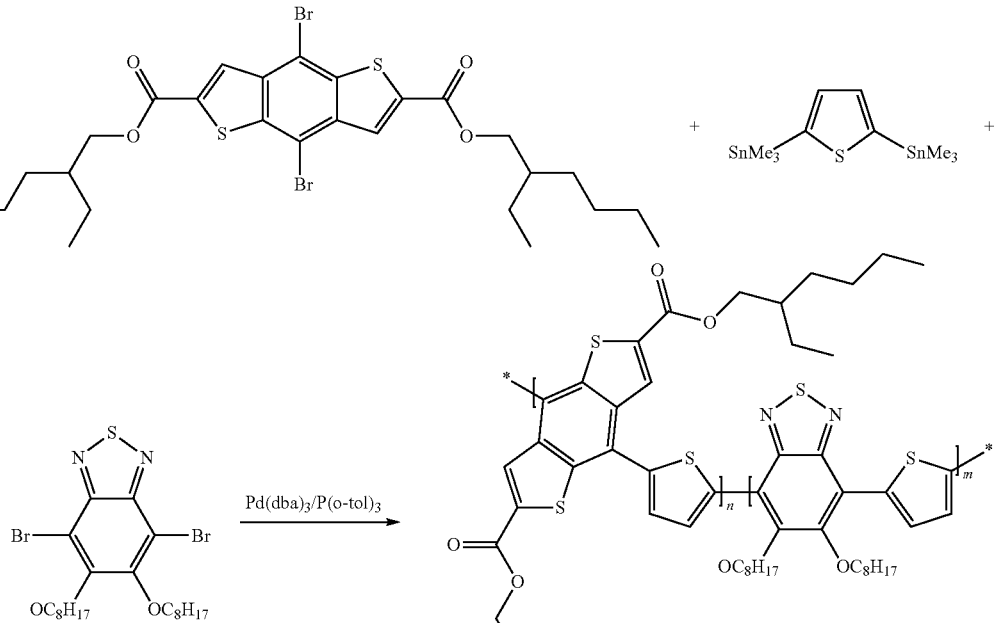

(1)

A solution of 4,8-dibromo-benzo[1,2-b;4,5-b']dithiophene-2,6-dicarboxylic acid bis-(2-ethyl-hexyl) ester (198 mg, 0.30 mmol), 2,5-bis-trimethylstannanyl-thiophene (246 mg, 0.60 mmol), 4,7-dibromo-5,6-bis-octyloxy-benzo[1,2,5]thiadiazole (165 mg, 0.30 mmol), tri(o-tolyl)phosphine (15 mg, 0.048 mmol) and tris(dibenzyl-ideneacetone)dipalladium(0) (11 mg, 0.01 mmol) in chlorobenzene (10 cm³) is prepared in a microwave tube. The mixture purged with nitrogen for 5 minutes. The reaction mixture is placed in a microwave reactor (Intitiator, Biotage AB) and heated sequentially at 140° C. (60 seconds), 160° C. (60 seconds), 170° C. (30 seconds) and 180° C. (1800 seconds). The reaction mixture is allowed to cool to 50° C. and precipitated into a stirred mixture of concentrated hydrochloric acid (10 cm³) and methanol (100 cm³) with methanol washings (2×10 cm³) of the reaction tube. The mixture is stirred for 10 minutes. The polymer collected by filtration and washed with methanol (100 cm³) to give a purple/black solid. The crude polymer is washed via Soxhlet extraction with acetone, 40-60 petrol and cyclohexane. The cyclohexane extract is precipitated into stirred methanol (200 cm³). The polymer collected by filtration and dried under vacuum to give poly{4,7-5,6-bis-octyloxy-benzo[1,2,5]thiadiazole}-co-{2,5-thienyl}-co-{4,8-benzo[1,2-b;4,5-b']dithiophene-2,6-dicarboxylic acid bis-(2-ethyl-hexyl) ester} as a black solid (60 mg, 19%). GPC (chlorobenzene, 50° C.) $M_n$=6,700 g/mol, $M_w$=10,500 g/mol, PD=1.55.

Example 2

Poly{1-(4,6-thieno[3,4-b]thiophen-2-yl)-2-ethyl-hexan-1-one}-co-{2,5-thienyl}-co-{4,8-benzo[1,2-b;4,5-b']dithiophene-2,6-dicarboxylic acid bis-(2-ethyl-hexyl) ester} (2)

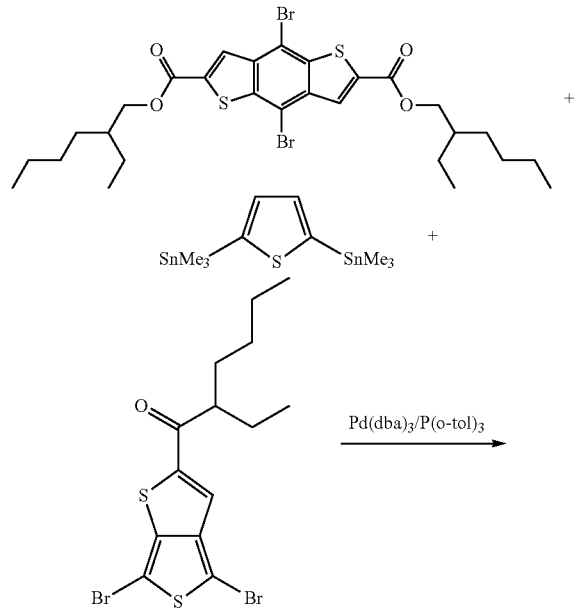

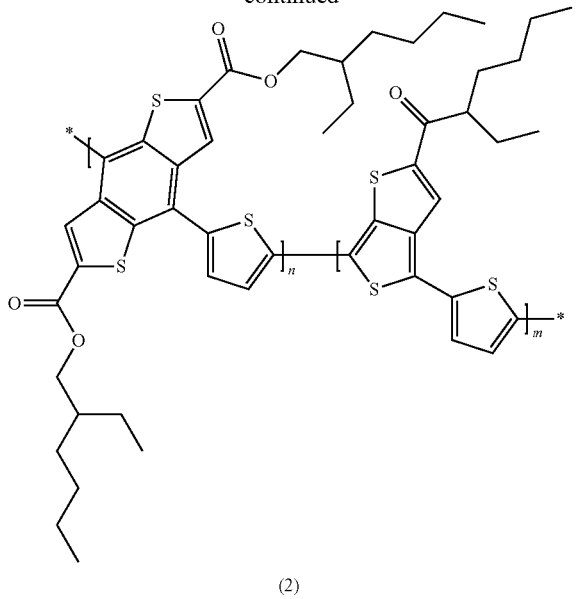

(2)

A solution of 4,8-dibromo-benzo[1,2-b;4,5-b']dithiophene-2,6-dicarboxylic acid bis-(2-ethyl-hexyl) ester (528 mg, 0.80 mmol), 2,5-bis-trimethylstannanyl-thiophene (655 mg, 1.60 mmol), 1-(4,6-dibromo-thieno[3,4-b]thiophen-2-yl)-2-ethyl-hexan-1-one (339 mg, 0.80 mmol), tri(o-tolyl) phosphine (39 mg, 0.13 mmol) and tris(dibenzyl-ideneacetone)dipalladium(0) (29 mg, 0.03 mmol) in chlorobenzene (15 cm³) is prepared in a microwave tube. The mixture purged with nitrogen for 5 minutes. The reaction mixture is placed in a microwave reactor (Intitiator, Biotage AB) and heated sequentially at 140° C. (60 seconds), 160° C. (60 seconds) and 170° C. (1800 seconds). The reaction mixture is allowed to cool to 60° C. and precipitated into a stirred mixture of concentrated hydrochloric acid (10 cm³) and methanol (100 cm³) with methanol washings (2×10 cm³) of the reaction tube. The mixture is stirred for 10 minutes. The polymer collected by filtration and washed with methanol (100 cm³) to give a black solid. The crude polymer is washed via Soxhlet extraction with acetone, methanol, 40-60 petrol, cyclohexane and chloroform. The chloroform extract is concentrated in vacuo and precipitated into stirred methanol (200 cm³). The polymer collected by filtration and dried under vacuum to give poly{1-(4,6-thieno[3,4-b]thiophen-2-yl)-2-ethyl-hexan-1-one}-co-{2,5-thienyl}-co-{4,8-benzo[1,2-b;4,5-b']dithiophene-2,6-dicarboxylic acid bis-(2-ethyl-hexyl) ester} as a black solid (600 mg, 81%). GPC (chlorobenzene, 50° C.) $M_n$=10,300 g/mol, $M_w$=35,500 g/mol, PD=3.43.

Example 3—Photovoltaic Device Fabrication and Measurement

A bulk heterojunction organic photovoltaic device (OPV) is fabricated according to the following procedure.

Patterned indium tin oxide (ITO) coated glass substrates (Luminescence Technology Corp.) are used as a transparent bottom electrode.

PEDOT:PSS (Clevios PVP AI4083, H. C. Stark) is blade coated from an aqueous solution onto the substrates and dried at 130° C. on a hotplate for 30 min. The resulting polymer layer is approximately 40 nm thickness.

A solution containing the polymer (1) from Example 1 and C61-PCBM (6,6-phenyl C61 butyric acid methyl ester, from Solenne BV) at a total solid concentration of 23 mg/cm$^3$ in o-dichlorobenzene and containing an additional 3% of diiodooctane is prepared; the active material ratio in the blend is 1:3 polymer to C61-PCBM. The blend is deposited by blade coating onto PEDOT:PSS layer and dried for 2 min at 70° C. The active layer thickness is about 140 nm.

The device is completed by depositing a top electrode material, Calcium (30 nm)/Aluminium (200 nm), by sequential thermal evaporation through a shadow mask.

Current-voltage characteristics were measured using a Keithley2400 SMU while the solar cells were illuminated by a Newport Solar Simulator at 100 mWcm$^{-2}$ white light. The Solar Simulator was equipped with AM1.5G filters. The illumination intensity was calibrated using a Si photodiode.

All the device preparation and characterisation is done in a dry-nitrogren atmosphere.

Power conversion efficiency is calculated using the following expression $$\eta = V_{oc} \times J_{sc} \times FF/P_{in}$$

where $FF$ is defined as $$FF = V_{max} \times J_{max}/V_{oc} \times J_{sc}$$

The following device performance is obtained. $V_{oc}$=750 mV, $J_{sc}$=−4.23 mA, FF=0.31, $\eta$=0.98%.

Example 4—Photovoltaic Device Fabrication and Measurement

A bulk heterojunction organic photovoltaic device (OPV) is fabricated according to the following procedure.

Patterned indium tin oxide (ITO) coated glass substrates (Luminescence Technology Corp.) are used as a transparent bottom electrode.

PEDOT:PSS (Clevios PVP AI4083, H. C. Stark) is blade coated from an aqueous solution onto the substrates and dried at 130° C. on a hotplate for 30 min. The resulting polymer layer is approximately 40 nm thickness.

A solution containing the polymer (2) from Example 2 and C61-PCBM (6,6-phenyl C61 butyric acid methyl ester, from Solenne BV) at a total solid concentration of 23 mg/cm$^3$ in o-dichlorobenzene and containing an additional 3% of diiodooctane is prepared; the active material ratio in the blend is 1:3 polymer to C61-PCBM. The blend is deposited by blade coating onto PEDOT:PSS layer and dried for 2 min at 70° C. The active layer thickness is about 115 nm.

The device is completed by depositing a top electrode material, Calcium (30 nm)/Aluminium (200 nm), by sequential thermal evaporation through a shadow mask.

Current-voltage characteristics were measured using a Keithley2400 SMU while the solar cells were illuminated by a Newport Solar Simulator at 100 mWcm$^{-2}$ white light. The Solar Simulator was equipped with AM1.5G filters. The illumination intensity was calibrated using a Si photodiode.

All the device preparation and characterisation is done in a dry-nitrogren atmosphere.

Power conversion efficiency is calculated using the following expression $$\eta = V_{oc} \times J_{sc} \times FF/P_{in}$$

where $FF$ is defined as $$FF = V_{max} \times J_{max}/V_{oc} \times J_{sc}$$

The following device performance is obtained. $V_{oc}$=630 mV, $J_{sc}$=−1.41 mA, FF=0.40, $\eta$=0.36%.

The invention claimed is:

1. Monomer of formula Ia $$R^2\text{-A-}R^3 \qquad \text{Ia}$$

wherein
A is a unit of formula I

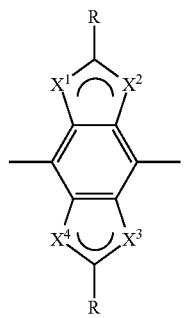

wherein
one of $X^1$ and $X^2$ is selected from S, Se and O, and the other is selected from CH, CR$^x$, and N,
one of $X^3$ and $X^4$ is selected from S, Se and O, and the other is selected from CH, CR$^x$, and N,
R on each occurrence identically or differently denotes
primary alkyl with 1 to 30 C atoms, wherein one or more H atoms are optionally replaced by F;
secondary alkyl with 3 to 30 C atoms, wherein one or more H atoms are optionally replaced by F;
tertiary alkyl with 4 to 30 C atoms, wherein one or more H atoms are optionally replaced by F;
—CO—R$^y$;
—CO—O—R$^y$ or
—O—CO—R$^y$,
R$^y$ is straight-chain, branched or cyclic alkyl with 1 to 30 C atoms, in which one or more non-adjacent C atoms are optionally replaced by —O—, —S—, —CO—, —CO—O—, —O—CO—, —O—CO—O—, —CR$^0$═CR$^{00}$— or —C≡C— and in which one or more H atoms are optionally replaced by F,
or
aryl or hetaryl having 2 to 30 C atoms that is unsubstituted or substituted by one or more non-aromatic groups R$^1$,
R$^x$ is on each occurrence identically or differently straight-chain, branched or cyclic alkyl with 1 to 15 C atoms, in which one or more non-adjacent C atoms are optionally replaced by —O—, —S—, —CO—, —CO—O—, —O—CO—O—, —CR$^0$═CR$^{00}$— or —C≡C— and in which one or more H atoms are optionally replaced by F, Cl, Br, I or CN,
R$^0$ and R$^{00}$ are independently of each other H or optionally substituted carbyl or hydrocarbyl optionally comprising one or more hetero atoms, and
R$^2$ and R$^3$ independently of each other denote Cl, Br, I, —B(OZ$^2$)$_2$, —CZ$^3$═C(Z$^4$)$_2$ or Sn(Z$^4$)$_3$, wherein Z$^{2-4}$ are selected from the group consisting of alkyl and aryl, each being optionally substituted, and two Z$^2$ groups may also form a cyclic group
R$^1$ is on each occurrence identically or differently H, halogen, —CN, —NC, —NCO, —NCS, —OCN, —SCN, —C(═O)NR$^0$R$^{00}$, —C(═O)X$^0$, —C(═O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms,
$X^o$ is halogen.

2. A monomer according to claim 1, wherein in the unit of formula I, $X^1$ and $X^3$ are S, and $X^2$ and $X^4$ are CH.

3. A monomer according to claim 1 wherein R or $R^y$ on each occurrence identically or differently denotes
   primary alkyl with 1 to 30 C atoms, wherein one or more H atoms are optionally replaced by F;
   secondary alkyl with 3 to 30 C atoms, wherein one or more H atoms are optionally replaced by F; or
   tertiary alkyl with 4 to 30 C atoms, wherein one or more H atoms are optionally replaced by F.

4. A monomer according to claim 1 wherein R on each occurrence identically or differently denotes
   —CO—$R^y$;
   —CO—O—$R^y$ or
   —O—CO—$R^y$
   and $R^y$ on each occurrence identically or differently denotes primary alkyl with 1 to 30 C atoms, wherein one or more H atoms are optionally replaced by F;
   secondary alkyl with 3 to 30 C atoms, wherein one or more H atoms are optionally replaced by F; or
   tertiary alkyl with 4 to 30 C atoms, wherein one or more H atoms are optionally replaced by F.

* * * * *